United States Patent [19]

Rohr et al.

[11] Patent Number: 4,565,565
[45] Date of Patent: Jan. 21, 1986

[54] DICHLOROACETAMIDES, HERBICIDES CONTAINING ACETANILIDES AS HERBICIDAL ACTIVE INGREDIENTS AND THE DICHLOROACETAMIDES AS ANTAGONISTS, AND THE USE OF THESE HERBICIDES IN CONTROLLING UNDESIRED PLANT GROWTH

[75] Inventors: Wolfgang Rohr, Wachenheim; Hanspeter Hansen; Peter Plath, both of Ludwigshafen; Bruno Wuerzer, Otterstadt, all of Fed. Rep. of Germany

[73] Assignee: BASF Aktiengesellschaft, Fed. Rep. of Germany

[21] Appl. No.: 519,821

[22] Filed: Aug. 3, 1983

Related U.S. Application Data

[62] Division of Ser. No. 207,337, Nov. 17, 1980, Pat. No. 4,448,960.

[30] Foreign Application Priority Data

Dec. 3, 1979 [DE] Fed. Rep. of Germany ....... 2948535

[51] Int. Cl.$^4$ ..................... A01N 43/48; A01N 37/18
[52] U.S. Cl. ........................................... 71/92; 71/118
[58] Field of Search ................................... 71/92, 118

[56] References Cited

U.S. PATENT DOCUMENTS

| | | | |
|---|---|---|---|
| 4,021,224 | 5/1977 | Pallos et al. | 71/118 |
| 4,124,376 | 11/1978 | Pallos et al. | 71/118 |
| 4,269,618 | 5/1981 | Pallos et al. | 71/118 |
| 4,272,282 | 6/1981 | Hansen et al. | 71/92 |
| 4,392,884 | 7/1983 | Pallos et al. | 71/118 |
| 4,396,416 | 8/1983 | Riebel et al. | 71/92 |
| 4,517,011 | 5/1985 | Thomas et al. | 71/92 |

*Primary Examiner*—Glennon H. Hollrah
*Assistant Examiner*—Raymond Covington
*Attorney, Agent, or Firm*—Keil & Weinkauf

[57] ABSTRACT

Novel dichloroacetamides of the formula (I)

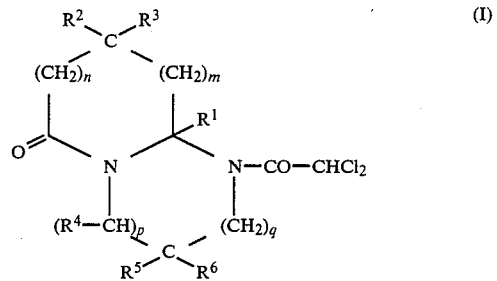

where $R^1$, $R^2$, $R^3$, $R^4$, $R^5$, $R^6$, m, n, p and q have the meanings given in the description.

The compounds are antagonists which increase the toleration, by crops, of herbicidal acetanilides. Herbicides containing the dichloroacetamides of the formula I in combination with acetanilides may be used for controlling undesired plant growth in Indian corn and cereals.

12 Claims, No Drawings

DICHLOROACETAMIDES, HERBICIDES CONTAINING ACETANILIDES AS HERBICIDAL ACTIVE INGREDIENTS AND THE DICHLOROACETAMIDES AS ANTAGONISTS, AND THE USE OF THESE HERBICIDES IN CONTROLLING UNDESIRED PLANT GROWTH

This is a division of application Ser. No. 207,337, filed Nov. 17, 1980, now U.S. Pat. No. 4,448,960.

The present invention relates to novel dichloroacetamides, a process for their preparation, herbicides containing acetanilides as herbicidal active ingredients and the dichloroacetamides as antagonists, and processes for the selective control of undesired plant growth by means of these herbicides.

Acetanilides of the formula II

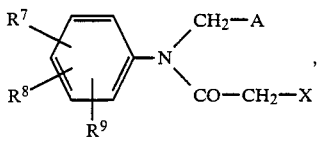

where
- $R^7$ is hydrogen or linear or branched alkyl or alkoxy of up to 5 carbon atoms,
- $R^8$ is hydrogen, halogen or linear or branched alkyl or alkoxy of up to 5 carbon atoms,
- $R^9$ is hydrogen, halogen or linear or branched alkyl or alkoxy of up to 5 carbon atoms,
- $R^7$ together with $R^8$ may also be alkylene of up to 6 carbon atoms which is ortho-linked to the benzene ring and is unsubstituted or substituted by linear or branched alkyl of up to 4 carbon atoms,
- X is chlorine or bromine and
- A is alkoxy or alkoxyalkyl of up to 4 carbon atoms, or is an azole radical which is bonded via a ring nitrogen and which may be monosubstituted or polysubstituted by halogen, phenyl, alkyl, alkoxy, alkylthio or perfluoroalkyl, each of up to 4 carbon atoms, cyano, carboxyl or alkoxycarbonyl, where alkoxy is of up to 4 carbon atoms, and may also be a salified azole radical, if the azole ring contains 2 or 3 nitrogens, are excellent herbicides but, when used in crops such as Indian corn, or in other graminaceous crops, lead to damage of the crop plants (German Laid-Open Applications Nos. DOS 2,648,008 and DOS 2,744,396).

It is an object of the present invention to provide antagonists which compensate for this non-toleration of the herbicidal acetanilides by certain crop plants.

Herbicides which in addition to herbicidal active ingredients contain dichloroacetamides as antagonists are disclosed in German Laid-Open Applications Nos. DOS 2,218,097 and DOS 2,245,471. The dichloroacetamides described in German Laid-Open Application No. DOS 2,218,097 are in the main used to prevent crop plant damage by thiolcarbamates, whilst German Laid-Open Application No. DOS 2,245,471 also discloses herbicides which contain dichloroacetamides and chloroacetanilides, eg. 2-chloro-2',6'-diethyl-N-butoxymethylacetanilide or 2-chloro-2',6'-diethyl-N-methoxymethylacetanilide.

We have found that dichloroacetamides of the formula (I)

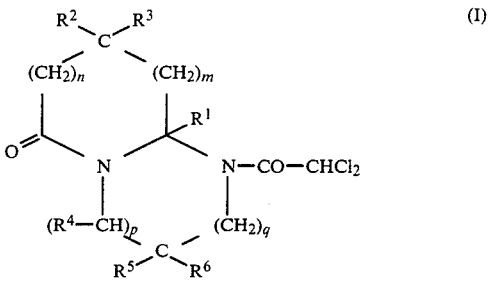

where
- $R^1$ is hydrogen, methyl or ethyl,
- $R^2$ and $R^3$ are identical or different and are hydrogen, methyl or methoxy,
- $R^4$ is hydrogen or methyl and
- $R^5$ and $R^6$ are identical or different and are hydrogen or methyl, and
- m is 0 or 1, n is 1 or 2, p is 0, 1 or 2 and q is 0, 1 or 2, are exceptionally suitable for improving the toleration of herbicidal acetanilides of the formula II by crop plants. Herbicides which contain an acetanilide of the formula II and a dichloroacetamide of the formula I may be used in Indian corn and cereals. The herbicidal effectiveness of the acetanilides is retained, whilst damage to the crop plants is suppressed.

Suitable antagonists are dichloroacetamides of diazabicycloalkanes, of the formula I, where $R^1$ is hydrogen, methyl or ethyl, $R^2$ and $R^3$ are identical or different and are hydrogen, methyl or methoxy, $R^4$ is hydrogen or methyl and $R^5$ and $R^6$ are identical or different and are hydrogen or methyl, and m is 0 or 1, n is 1 or 2, p is 0, 1 or 2 and q is 0, 1 or 2. Preferably, $R^1$ is methyl, $R^2$, $R^3$, $R^4$, $R^5$ and $R^6$ are hydrogen, m is 0 and n, p and q are 1.

Examples of antidotes of the formula I are 4-dichloroacetyl-8-oxo-1,4-diaza-bicyclo[3.3.0]octane, 4-dichloroacetyl-5-methyl-8-oxo-1,4-diazabicyclo[3.3.0]octane, 4-dichloroacetyl-5-ethyl-8-oxo-1,4-diazabicyclo[3.3.0]octane, 5-dichloroacetyl-9-oxo-1,5-diazabicyclo[4.3.0]nonane, 5-dichloroacetyl-6-methyl-9-oxo-1,5-diazabicyclo[4.3.0]nonane, 5-dichloroacetyl-6-ethyl-9-oxo-1,5-diazabicyclo[4.3.0]nonane, 6-dichloroacetyl-7-methyl-10-oxo-1,6-diazabicyclo[5.3.0]decane, 7-dichloroacetyl-2-oxo-1,7-diazabicyclo[4.3.0]nonane, 7-dichloroacetyl-6-methyl-2-oxo-1,7-diazabicyclo[4.3.0]nonane, 7-dichloroacetyl-6-methyl-2-oxo-1,7-diazabicyclo[4.4.0]decane, 5-dichloroacetyl-3,3,6-trimethyl-9-oxo-1,5-diazabicyclo[4.3.0]nonane, 5-dichloroacetyl-4,4,6-trimethyl-9-oxo-1,5-diazobicyclo[4.3.0]nonane, 5-dichloroacetyl-4,4,6-trimethyl-10-oxo-1,5-diazabicyclo[4.4.0]decane, 5-dichloroacetyl-3,3,6-trimethyl-10-oxo-1,5-diazabicyclo[4.4.0]decane, 7-dichloroacetyl-5-methoxy-6-methyl-2-oxo-1,7-diazabicyclo[4.3.0]nonane, 5-dichloroacetyl-3,3-dimethyl-9-oxo-1,5-diazabicyclo[4.3.0]nonane and 5-dichloroacetyl-6-methyl-7-methoxy-10-oxo-1,5-diazabicyclo[4.4.0]decane. Preferred antagonists are 4-dichloroacetyl-5-methyl-8-oxo-1,4-diazabicyclo[3.3.0]octane, 5-dichloroacetyl-6-methyl-9-oxo-1,5-diazabicyclo[4.3.0]nonane and 5-dichloroacetyl-3,3,6-trimethyl-9-oxo-1,5-diazabicyclo[4.3.0]nonane.

The dichloroacetamides of the formula I may be prepared in a conventional manner by reacting a diazobicycloalkane of the formula III

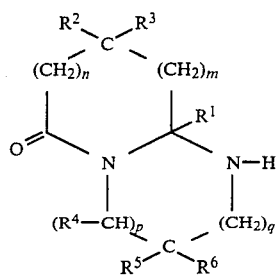

(III)

where $R^1$, $R^2$, $R^3$, $R^4$, $R^5$, $R^6$, m, n, p and q have the above meanings, with dichloroacetyl chloride. The reaction is carried out in a solvent or diluent, in the presence of a hydrogen chloride acceptor, at from $-10°$ to $+20°$ C. In general, the starting materials are employed in the equimolar ratio; however, it is also possible to use an excess of dichloroacetyl chloride.

Suitable diluents and solvents are hydrocarbons and halohydrocarbons, eg. toluene, xylenes, chlorobenzene, methylene chloride and ethylene chloride, ethers, eg. diethyl ether, methyl tert.-butyl ether, tetrahydrofuran and 1,4-dioxane, and nitriles, eg. acetonitrile.

Suitable hydrogen chloride acceptors are alkali metal carbonates, alkali metal bicarbonates, alkali metal hydroxides, trialkylamines, N,N-dialkylanilines and pyridine bases.

The dichloroacetamides according to the invention may also be prepared by reacting a diazabicycloalkane of the formula III with chloral hydrate in the presence of an acid acceptor and of a catalytic amount of a cyanide, which is, for example, added in the form of sodium cyanide or of acetone cyanohydrin (German Laid-Open Application No. DOS 2,807,340).

Some of the bicyclic amines of the formula III are disclosed in German Laid-Open Application No. DOS 1,802,468. They may be prepared by the process described there, namely reaction of a γ-oxo- or δ-oxo-carboxylic acid, or of an ester thereof, with an α,ω-alkylenediamine. For example, 6-methyl-9-oxo-1,5-diazabicyclo[4.3.0]nonane may be prepared from ethyl levulate and propylenediamine.

The Example which follows illustrates the preparation of a novel dichloroacetamide of the formula I.

EXAMPLE 10.5 g (0.105 mole) of triethylamine are added to a solution of 15.4 g (0.1 mole) of 6-methyl-9-oxo-1,5-diazabicyclo[4.3.0]nonane in 100 ml of toluene. The mixture is cooled to $-10°$ C. and 14.8 g (0.1 mole) of dichloroacetyl chloride are added dropwise at from $-10°$ to $-5°$ C. The batch is stirred for a further 4 hours and the triethylamine hydrochloride which has precipitated is filtered off. After evaporating the toluene from the filtrate, crystals separate out, and these can be recrystallized from a 1:3 toluene/acetone mixture. 17.7 g of 5-dichloroacetyl-6-methyl-9-oxo-1,5-diazabicyclo[4.3.0]nonane, of melting point 144°–147° C., are obtained.

The dichloroacetamides tabulated below may be obtained in a similar manner. Where the compound is liquid under normal conditions, it may be necessary to purify it chromatographically over silica gel (using a 1:3 mixture of ethyl acetate/acetone or toluene/acetone as the mobile phase).

| No. | Formula | Melting point [°C.] |
|---|---|---|
| 1 | (R=H, 5-ring) | 110 |
| 2 | (R=CH₃, 5-ring) | 119–121 |
| 3 | (R=C₂H₅, 5-ring) | Oil |
| 4 | (R=H, 6-ring) | 130 |
| 5 | (R=C₂H₅, 6-ring) | Oil |
| 6 | (R=CH₃, 6-ring) | |
| 7 | (R=H, 7-ring) | |
| 8 | (R=CH₃, 7-ring) | 113–115 |
| 9 | (R=CH₃, 6-ring variant) | 125 |
| 10 | (R=CH₃, with gem-dimethyl) | 151–152 |

-continued

| No. | Formula | Melting point [°C.] |
|---|---|---|
| 11 | (structure: piperidinone with CH₃, N—CO—CHCl₂, and C(CH₃)₂CH₂ substituents) | 162–164 |
| 12 | (structure: piperidinone with CH₃, N—CO—CHCl₂, and CH₂C(CH₃)₂ substituents) | |
| 13 | (structure: piperidinone ring with CH₃, N—CO—CHCl₂, C(CH₃)₂) | |
| 14 | (structure with OCH₃, CH₃, N—CO—CHCl₂) | Oil |
| 15 | (structure with OCH₃, CH₃, N—CO—CHCl₂) | 137–139 |
| 16 | (structure with CH₃, N—CO—CHCl₂, CH₃) (Isomer mixture) | |
| 17 | (structure with CH₃, N—CO—CHCl₂, H₃C and CH₃) | 132–133 |
| 18 | (structure with CH₃, N—CO—CHCl₂, CH₃) (Isomer mixture) | |
| 19 | (structure with CH₃, N—CO—CHCl₂, H₃C and CH₃) | |
| 20 | (structure: pyrrolidinone with CH₃, N—CO—CHCl₂, C(CH₃)₂) | 146 |

Acetanilides whose toleration by crop plants can be improved by the novel dichloroacetamides of the formula I are compounds of the formula II where $R^7$ is hydrogen, alkyl of up to 5 carbon atoms, eg. methyl, ethyl, n-propyl, i-propyl, n-butyl, sec.-butyl, i-butyl, tert.-butyl or normal or branched pentyl, or alkoxy of up to 5 carbon atoms, eg. methoxy, ethoxy, propoxy, butoxy or pentoxy, $R^8$ and $R^9$ are hydrogen, halogen, eg. fluorine, chlorine, bromine or iodine, alkyl of up to 5 carbon atoms, eg. methyl, ethyl, n-propyl, i-propyl, n-butyl, sec.-butyl, i-butyl, tert.-butyl or normal or branched pentyl, or alkoxy of up to 5 carbon atoms, eg. methoxy, ethoxy, propoxy, butoxy or pentoxy, $R^7$ together with $R^8$ may also be alkylene of up to 6 carbon atoms which is ortho-linked to the benzene ring and is unsubstituted or substituted by alkyl of up to 4 carbon atoms, eg. ethylene, trimethylene, tetramethylene, 1-methyl-trimethylene, 1,1-dimethyl-trimethylene or 1,1-dimethyl-tetramethylene, X is chlorine or bromine, preferably chlorine, and A is an azole radical, eg. a pyrrole, pyrazole, imidazole, 1,2,4-triazole, 1,2,3-triazole or tetrazole radical, which is bonded via a ring nitrogen and may be monosubstituted or polysubstituted by halogen, phenyl, alkyl, alkoxy, alkylthio or perfluoroalkyl, each of up to 4 carbon atoms, cyano, carboxyl, or alkoxycarbonyl, where alkoxy is of up to 4 carbon atoms, or is alkoxy or alkoxyalkyl of up to 4 carbon atoms, eg. methoxy, ethoxy, methoxymethyl and 2-methoxyethyl.

Examples of substituted azole radicals A are the radicals of 2,6-dimethyl-pyrrole, tetramethylpyrrole, 3(5)-methylpyrazole, 4-methylpyrazole, 3(5)-ethylpyrazole, 4-ethylpyrazole, 3(5)-isopropylpyrazole, 4-isopropylpyrazole, 3,5-dimethylpyrazole, 3,4,5-trimethylpyrazole, 3(5)-phenylpyrazole, 4-phenylpyrazole, 3,5-diphenylpyrazole, 3(5)-phenyl-5(3)-methylpyrazole, 3(5)-chloropyrazole, 4-chloropyrazole, 4-bromopyrazole, 3,5-dimethyl-4-chloropyrazole, 3,5-dimethyl-4-bromopyrazole, 4-chloro-3(5)-methylpyrazole, 4-methyl-3,5-dichloropyrazole, 3(5)-methyl-4,5(3)-dichloropyrazole, 3(5)-chloro-5(3)-methylpyrazole, 4-methoxypyrazole, 3(5)-methyl-5(3)-trifluoromethylpyrazole, 3(5)-methyl-5(3)-ethoxycarbonylpyrazole, 3(5)-methyl-5(3)-methylthio-4-methoxycarbonylpyrazole, 4-cyanopyrazole, 4,5-dichloroimidazole, 2-methyl-4,5-dichloroimidazole, 3(5)-methyl-1,2,4-triazole, 3,5-dimethyl-1,2,4-triazole, 3(5)-chloro-1,2,4-triazole, 3,5-dichloro-1,2,4-triazole, 4(5)-methyl-1,2,3-triazole, 5-methyltetrazole and 5-chlorotetrazole.

Furthermore, azole radicals A which contain 2 or 3 nitrogens may also be salified with a conventional strong inorganic or organic acid, eg. hydrochloric acid, nitric acid, sulfuric acid, trichloroacetic acid, methanesulfonic acid, perfluorohexanesulfonic acid or dodecylbenzenesulfonic acid.

Preferred acetanilides of the formula II are those in which the phenyl ring carries methyl or ethyl in the 2- and 6-positions and hydrogen or methyl in the 3-position. X is preferably chlorine, whilst A is, in particular, an azole radical, eg. the radical of pyrazole, 4-methylpyrazole, 4-methoxypyrazole, 3-methylpyrazole, 3,5-dimethylpyrazole, 1,2,4-triazole or 4,5-dichloroimidazole, or is ethoxy or methoxymethyl.

In particular, the following acetanilides may for example be present in the novel herbicides: 2-chloro-2',6'-dimethyl-N-(pyrazol-1-yl-methyl)-acetanilide, 2-chloro-2'-methyl-6'-ethyl-N-(pyrazol-1-yl-methyl)-acetanilide, 2-chloro-2',6'-dimethyl-N-(4-methyl-pyrazol-1-yl-methyl)-acetanilide, 2-chloro-2'-methyl-6'-ethyl-N-(4-methoxy-pyrazol-1-yl-methyl)-acetanilide, 2-chloro-2',6'-dimethyl-N-(3,5-dimethylpyrazol-1-yl-methyl)-acetanilide, 2-chloro-2'-methyl-6'-ethyl-N-(3-methyl-pyrazol-1-yl-methyl)-acetanilide, 2-chloro-2',6'-dimethyl-N-(1,2,4-triazol-1-yl-methyl)-acetanilide, 2-chloro-2',3',6'-trimethyl-N-(pyrazol-1-yl-methyl)-acetanilide, 2-chloro-2'-methyl-6'-ethyl-N-(3,5-dimethyl-pyrazol-1-yl-methyl)-acetanilide, 2-chloro-2',6'-diethyl-N-(3,5-dimethyl-pyrazol-1-yl-methyl)-acetanilide, 2-chloro-2',3',6'-trimethyl-N-(3,5-dimethyl-pyrazol-1-yl-methyl)-acetanilide, 2-chloro-2',6'-diethyl-N-(pyrazol-1-yl-methyl)-acetanilide, 2-chloro-2',6'-dimethyl-N-(4,5-dichloroimidazol-1-yl-methyl)-acetanilide, 2-chloro-2'-methyl-6'-ethyl-N-(4,5-dichloroimidazol-1-yl-methyl)-acetanilide, 2-chloro-2',6'-diethyl-N-(4,5-dichloroimidazol-1-yl-methyl)-acetanilide, 2-chloro-2'-methyl-6'-ethyl-N-(1,2,4-triazol-1-yl-methyl)-acetanilide, 2-chloro-2',6'-diethyl-N-(1,2,4-triazol-1-yl-methyl)-acetanilide, 2-chloro-2',3',6'-trimethyl-N-(1,2,4-triazol-1-yl-methyl)-acetanilide, 2-chloro-2',6'-dimethyl-N-(2-methoxy-ethyl)-acetanilide and 2-chloro-2'-methyl-6'-ethyl-N-ethoxymethylacetanilide.

The acetanilides of the formula II, and their preparation, form the subject of German Laid-Open Applications Nos. DOS 2,648,008, DOS 2,744,396 and DOS 2,305,495, and of U.S. Pat. No. 3,547,620.

The herbicidal active ingredients and the antagonists may be incorporated into the soil conjointly or separately, before or after sowing. The most common method of using the acetanilides is to apply them to the surface of the soil immediately after sowing, or during the period between sowing and emergence. Treatment during emergence is also possible. In each of these cases, the antagonist may be applied simultaneously with the herbicide or separately, the antagonist being applied first and the herbicide subsequently, or vice versa, provided in the latter case that the time which elapses before the antagonist is applied is not so great that the herbicide has already damaged the crop. The active ingredient and antagonist may be formulated, separately or conjointly, as a suspendable, emulsifiable or soluble spraying agent, or as granules. It is also conceivable to treat the crop seed with the antagonist before sowing. In that case the herbicide is applied by itself, in a conventional manner.

For a given herbicidal acetanilide, different amounts of antagonist are required for different crops. The ratios in which the acetanilide and dichloroacetamide are employed can be varied within a wide range and depend on the structure of the acetanilide and of the dichloroacetamide and, as already stated, on the particular crop. Suitable ratios, by weight, of herbicidal active ingredient to antagonist are from 1:2 to 1:0.01, preferably from 1:0.25 to 1:0.05.

In addition to the acetanilide and the dichloroacetamide, the novel herbicides may contain other herbicides or growth regulators of a different chemical structure, for example 2-chloro-4-ethylamino-6-isopropylamino-1,3,5-triazine, without such additives affecting the antagonistic action.

The agents according to the invention, or—where applied separately—the herbicidal active ingredients and the antidote, are applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the herbicidal active ingredient and/or antidote as such or dissolved in an oil or solvent may be homogenized in water by means of wetting or dispersing agents, adherents or emulsifiers. Concentrates which are suitable for dilution with water may be prepared from active ingredient and/or antidote, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the herbicidal active ingredient and/or antidote with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of herbicidal active ingredient and antidote. Application rates are from 0.2 to 5 kg of herbicidal active ingredient per hectare. This amount of herbicidal active ingredient is applied, conjointly or separately, with such an amount of antidote that the ratio of herbicidal active ingredient to antagonistic compound is from 1:2 to 1:0.01, preferably from 1:0.25 to 1:0.05, parts by weight.

Examples of formulations are given below.

I. 40 parts by weight of a composition of 4 parts by weight of 2-chloro-2',6'-dimethyl-N-(pyrazol-1-yl-methyl)-acetanilide and 1 part by weight of 5-dichloroacetyl-6-methyl-9-oxo-1,5-diazobicyclo[4.3.0]nonane is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

II. 3 parts by weight of a composition of 1 part by weight of 2-chloro-2',6'-dimethyl-N-(pyrazol-1-yl-methyl)-acetanilide and 1 part by weight of 4-dichloroacetyl-5-methyl-8-oxo-1,4-diazobicyclo[3.3.0]octane is intimately mixed with 97 parts by weight of particulate kaolin. A dust is obtained containing 3% by weight of the active ingredient.

III. 30 parts by weight of a composition of 1 part by weight of 2-chloro-2'-methyl-6'-ethyl-N-(1,2,4-triazol-1-yl-methyl)-acetanilide and 2 parts by weight of 5-dichloroacetyl-3,3,6-trimethyl-9-oxo-1,5-diazobicyclo[4.3.0]nonane is intimately mixed with a mixture consisting of 92 parts by weight of powdered silica gel and 8 parts by weight of paraffin oil which has been sprayed onto the surface of this silica gel. A formulation of the active ingredient is obtained having good adherence.

IV. 20 parts by weight of a composition of 8 parts by weight of 2-chloro-2'-methyl-6'-ethyl-N-ethoxymethylacetanilide and 1 part by weight of 5-dichloroacetyl-4,4,6-trimethyl-9-oxo-1,5-diazobicyclo[4.3.0]nonane is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

V. 20 parts by weight of a composition of 10 parts by weight of 2-chloro-2',6'-dimethyl-N-(2-methoxyethyl)-acetanilide and 1 part by weight of 4-dichloroacetyl-5-methyl-8-oxo-1,4-diazobicyclo[3.3.0]octane is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

The influence of various representatives of herbicides according to the invention on the growth of unwanted and crop plants compared with that of herbicides consisting of the same herbicidal active ingredients and a prior art antagonistic compound of chemically similar structure is demonstrated in the following biological experiments. These experiments show that the tolerance of the herbicidal acetanilides by combined application with the novel dichloroacetamides is decisively improved and the herbicidal effectiveness retained, even under conditions, e.g., very heavy rainfall, posing difficulties to herbicides and plant growth.

The series of experiments were carried out in the greenhouse and in the open.

I. Greenhouse experiments

Plastic boxes 51 cm long, 32 cm wide and 6 cm deep were filled with loamy sand (pH: 6) containing about 1.5% humus. Indian corn (*Zea mays*) was sown shallow, in rows, in this substrate. *Echinochloa crus-galli* was scattered at random as unwanted plant. The non-sterilized soil also additionally contained viable weed seeds which contributed to the weed population. A field with crop plants growing in it and infested with weeds was thus simulated.

The active ingredients and antagonists were applied separately and in the mixtures given below. They were emulsified or suspended in water as vehicle and the liquor was sprayed through finely distributing nozzles onto the soil surface, either immediately after sowing or prior to emergence of the test plants. In some instances, the agents were also incorporated into the soil before the crop plants were sown. After sowing and treatment the boxes were sprinkler-irrigated and covered with transparent plastic hoods until the plants emerged. These measures ensured that the plants germinated and took root uniformly. The boxes were set up in the greenhouse at from 18° to 30° C.

These greenhouse experiments were monitored until 3 to 5 Indian corn leaves had developed. No more damage due to the herbicidal agents was to be expected after this stage, a fact confirmed by the experiments in the open.

The scale for assessing the action of the agents was 0 to 100, 0 denoting normal emergence and development of the plants, with reference to the untreated control, and 100 denoting non-germination or withering of the plants.

II. Experiments in the open

These experiments were run on small plots in loamy sand and loam (pH: 5 to 6) with a humus content of 1 to 1.5%. Preemergence treatment took place either immediately after the crop plants had been sown, or at the latest 3 days later. The weed flora was made up of various species and was naturally occurring. However, only the dominating representatives have been included in the tables. Active ingredients and antagonists, and combinations thereof, were emulsified or suspended in water as vehicle and applied by means of a motor-driven plot spray mounted on a tractor. Where no rain fell, the plots were sprinkled to ensure normal emergence of the crop plants and weeds.

In some of the experiments, importance was attached to particularly severe conditions for the herbicides—as a result of excess precipitate, the germination and root zones of the crop plants were particularly exposed to the action of the herbicidal acetanilides; the herbicides themselves were subjected to increased mobility in the soil. Assessment of the action of the agents was also made on the 0 to 100 scale.

The results tabulated below show that where the new antagonistic dichloroacetamides are applied on their own, they have a scarcely perceptible effect, if at all, on the germination and growth of the unwanted and crop plants. They are also herbicidally ineffective at application rates substantially higher than those required for antagonistic effects.

However, the new compounds reduce the phytotoxicity of the herbicidal acetanilides of the formula II to Indian corn to a considerable extent and in some cases eliminate it completely, even under unusual circumstances, e.g., heavy rainfall. It was found that in the case of herbicidal compounds which are less aggressive to crop plants it is sufficient to add smaller amounts of antagonistic compounds or antagonistic compounds having a lesser antagonistic action.

TABLE 1
List of plant names

| Botanical name | Abbreviation in tables | Common name |
|---|---|---|
| *Alopecurus myosuroides* | *Alopec. myos.* | slender foxtail |
| *Chenopodium album* | *Chenop. alb.* | lambsquarters |
| *Echinochloa crus galli* | *Echinochl. crus-galli* | barnyardgrass |
| *Zea mays* | | Indian corn |

TABLE 2
List of the herbicidal acetanilides employed in the examples

| Designation | A | $R^7$ | $R^8$ | $R^9$ |
|---|---|---|---|---|
| A | pyrazolyl | $CH_3$ | H | $CH_3$ |
| B | pyrazolyl | $C_2H_5$ | H | $CH_3$ |
| C | 3-methylpyrazolyl | $CH_3$ | H | $CH_3$ |
| D | 3-methoxypyrazolyl | $C_2H_5$ | H | $CH_3$ |
| E | 3-methylpyrazolyl | $C_2H_5$ | H | $CH_3$ |
| F | 3,5-dimethylpyrazolyl | $CH_3$ | H | $CH_3$ |
| G | 1,2,4-triazolyl | $CH_3$ | H | $CH_3$ |
| H | pyrazolyl | $CH_3$ | $CH_3$ | $CH_3$ |
| I | $-O-C_2H_5$ | $CH_3$ | H | $C_2H_5$ |
| K | $-CH_2-O-CH_3$ | $CH_3$ | H | $CH_3$ |

TABLE 3
List of the antagonistic compounds employed in the examples

| No. | Structural formula |
|---|---|
| $A_1$ | 1-(dichloroacetyl)-2-methyl-2-(pyrrolidin-1-yl derivative) |
| $A_2$ | (piperidine variant with $CH_3$, $N-CO-CHCl_2$) |
| $A_3$ | (piperidine with gem-dimethyl, $CH_3$, $N-CO-CHCl_2$) |

TABLE 3-continued

List of the antagonistic compounds employed in the examples

| No. | Structural formula |
|---|---|
| $A_4$ | (pyrrolidinone with N—CO—CHCl$_2$ substituent, gem-dimethyl) |
| $A_5$ | (pyrrolidinone with N—CO—CHCl$_2$ substituent) |
| $A_6$ | (piperidinone with CH$_3$ and N—CO—CHCl$_2$) |
| $A_7$ | (piperidinone with CH$_3$ and N—CO—CHCl$_2$) |
| $A_8$ | (morpholine with N—CO—CHCl$_2$) — (German Laid-Open Application DOS 2,218,097) |
| $A_9$ | (pyrrolidine with N—CO—CHCl$_2$) — (German Laid-Open Application DOS 2,245,471) |

TABLE 4

Reduction in the damage to Indian corn caused by 2-chloro-2',6'-dimethyl-N—(pyrazol-1-yl-methyl)-acetanilide as a result of the addition of antagonistic dichloroacetamides; preemergence treatment in the greenhouse

| Active ingredient | Antagonist | Appln. rate (kg a.i./ha) | Crop plant Zea mays | Unwanted plant Echinochloa crus-galli |
|---|---|---|---|---|
| | $A_1$ | 4.0 | 0 | 0 |
| | $A_2$ | 4.0 | 10 | 0 |
| | $A_3$ | 4.0 | 0 | 0 |
| A | — | 1.0 | 33 | 100 |
| | — | 2.0 | 85 | 100 |
| A | $A_1$ | 1.0 + 0.1 | 12 | 100 |
| | | 1.0 + 0.25 | 12 | 100 |
| | | 2.0 + 0.5 | 9 | 100 |
| A | $A_2$ | 1.0 + 0.1 | 8 | 100 |
| | | 1.0 + 0.25 | 0 | 99 |
| | | 2.0 + 0.5 | 10 | 100 |
| A | $A_3$ | 1.0 + 0.1 | 0 | 99 |
| | | 2.0 + 0.5 | 5 | 100 |
| A | $A_8$ (prior art) | 2.0 + 0.5 | 36 | 99 |
| A | $A_9$ (prior art) | 2.0 + 0.5 | 32 | 100 |

0 = normal emergence; no damage
100 = nonemergence, or plants destroyed

TABLE 5

Antagonistic action of a dichloroacetamide to prevent damage to Indian corn by 2-chloro-2',6'-dimethyl-N—(pyrazol-1-yl-methyl)-acetanilide under difficult conditions in the open

| Active ingredient | Antagonist | Appln. rate (kg a.i./ha) | Crop plant Zea mays | Alopec. myos. | Echinochl. crus-galli | Chenop. album |
|---|---|---|---|---|---|---|
| A | — | 1.0 | 26 | 100 | 100 | 97 |
| | | 2.0 | 65 | 100 | 100 | 99 |
| A | $A_1$ | 1.0 + 0.125 | 3 | 100 | 100 | 99 |
| | | 1.0 + 0.25 | 2 | 100 | 100 | 99 |
| | | 2.0 + 0.25 | 8 | 100 | 100 | 100 |
| | | 2.0 + 0.5 | 4 | 100 | 100 | 100 |

0 = no damage
100 = nonemergence, or plants destroyed

TABLE 6

Reduction in damage to Indian corn by herbicidal haloacetanilides as a result of the addition of an antagonistic dichloroacetamide; preemergence treatment in the greenhouse

| Active ingredient | Antagonist | Appln. rate (kg a.i./ha) | Crop plant Zea mays | Unwanted plant Echinochloa crus-galli |
|---|---|---|---|---|
| B | | 1.0 | 30 | 98 |
| | | 2.0 | 80 | 100 |
| B | $A_3$ | 1.0 + 0.125 | 0 | 100 |
| | | 2.0 + 0.5 | 0 | 100 |
| | | 2.0 + 0.25 | 0 | 100 |
| C | | 1.5 | 30 | 98 |
| | | 2.5 | 40 | 98 |
| C | $A_3$ | 1.5 + 0.188 | 5 | 100 |
| | | 2.5 + 0.625 | 0 | 100 |
| D | | 1.5 | 20 | 90 |
| | | 2.5 | 35 | 90 |
| D | $A_3$ | 1.5 + 0.188 | 0 | 95 |
| | | 2.5 + 0.625 | 10 | 98 |
| E | | 1.0 | 30 | 95 |
| E | $A_3$ | 1.0 + 0.125 | 0 | 100 |
| F | | 1.0 | 60 | 98 |
| F | $A_3$ | 1.0 + 0.125 | 10 | 100 |
| G | | 1.5 | 15 | 98 |
| | | 2.5 | 30 | 100 |
| G | $A_3$ | 1.5 + 0.188 | 0 | 95 |
| | | 2.5 + 0.313 | 0 | 95 |
| H | | 1.5 | 80 | 98 |
| H | $A_3$ | 1.5 + 0.188 | 10 | 100 |
| I | | 2.0 | 25 | 100 |
| I | $A_3$ | 2.0 + 0.25 | 0 | 100 |

TABLE 6-continued

Reduction in damage to Indian corn by herbicidal haloacetanilides as a result of the addition of an antagonistic dichloroacetamide; preemergence treatment in the greenhouse

| Active ingredient | Antagonist | Appln. rate (kg a.i./ha) | Test plants and % damage | |
|---|---|---|---|---|
| | | | Crop plant Zea mays | Unwanted plant Echinochloa crus-galli |
| K | " | 1.0 | 40 | 98 |
| K | $A_3$ | 1.0 + 0.125 | 0 | 98 |
| K | $A_9$ | 1.0 + 0.125 | 25 | 100 |
| | | 1.0 + 0.25 | 10 | 100 |

0 = normal emergence; no damage
100 = nonemergence, or plants destroyed

TABLE 7

Reduction in extremely heavy damage to Indian corn by 2-chloro-2',6'-dimethyl-N—(pyrazol-1-yl-methyl)-acetanilide as a result of the addition of antagonistic dichloroacetamides; preemergence treatment in the greenhouse

| Active ingredient | Antagonist | Appln. rate (kg a.i./ha) | Test plants and % damage | |
|---|---|---|---|---|
| | | | Crop plant Zea mays | Unwanted plant Echinochloa crus-galli |
| A | — | 1.0 | 70 | 100 |
| A | $A_4$ | 1.0 + 0.125 | 25 | 100 |
| A | $A_5$ | 1.0 + 0.25 | 15 | 100 |
| A | $A_6$ | 1.0 + 0.125 | 10 | 100 |
| A | $A_7$ | 1.0 + 0.125 | 10 | 100 |

0 = no damage
100 = nonemergence, or plants destroyed

We claim:

1. A herbicidal agent containing, as herbicidal active ingredient, an effective amount of at least one acetanilide of the formula $$\text{(II)}$$

where
$R^7$ is hydrogen or linear or branched alkyl or alkoxy of up to 5 carbon atoms,
$R^8$ is hydrogen, halogen or linear or branched alkyl or alkoxy of up to 5 carbon atoms,
$R^9$ is hydrogen, halogen or linear or branched alkyl or alkoxy of up to 5 carbon atoms,
$R^7$ together with $R^8$ may also be alkylene of up to 6 carbon atoms which is ortho-linked to the benzene ring and is unsubstituted or substituted by linear or branched alkyl of up to 4 carbon atoms,
X is chlorine or bromine and
A is alkoxy or alkoxyalkyl of up to 4 carbon atoms, or is an azole radical which is bonded via a ring nitrogen and which may be monosubstituted or polysubstituted by halogen, phenyl, alkyl, alkoxy, alkylthio or perfluoroalkyl, each of up to 4 carbon atoms, cyano, carboxyl or alkoxycarbonyl, where alkoxy is of up to 4 carbon atoms, and may also be a salified azole radical if the azole ring contains 2 or 3 nitrogens,
and, as antagonist, an effective amount of at least one dichloroacetamide of the formula $$\text{(I)}$$

where
$R^1$ is hydrogen, methyl or ethyl,
$R^2$ and $R^3$ are identical or different and are hydrogen, methyl or methoxy,
$R^4$ is hydrogen or methyl and
$R^5$ and $R^6$ are identical or different and are hydrogen or methyl, and
m is 0 or 1, n is 1 or 2, p is 0, 1 or 2 and q is 0, 1 or 2.

2. A herbicidal agent as claimed in claim 1, wherein the ratio of acetanilide to dichloroacetamide, applied conjointly or separately, is from 1:2 to 1:0.01 parts by weight.

3. A process for the selective control of unwanted plants, wherein the acetanilide of the formula II and the dichloroacetamide of the formula I as claimed in claim 1 are applied, simultaneously or one after the other in any sequence, before, during or after sowing of the crop plants, or before or during emergence of the crop plants.

4. A process for the selective control of unwanted plants with acetanilides of the formula II, wherein the crop plant seed is treated with a dichloroacetamide of the formula I as claimed in claim 1.

5. A process as set forth in claim 3 wherein the crop plant is a cereal.

6. A process as set forth in claim 4 wherein the crop plant is a cereal.

7. A herbicidal agent as set forth in claim 1, wherein the sum of p+q in the compound of formula I is 1 or 2.

8. A herbicidal agent as defined in claim 1, wherein the acetanilide of the formula II is selected from the group consisting of 2-chloro-2',6'-dimethyl-N-(pyrazol-1-yl-methyl)-acetanilide, 2-chloro-2'-methyl-6'-ethyl-N-(pyrazol-1-yl-methyl)-acetanilide, 2-chloro-2',6'-dimethyl-N-(4-methyl-pyrazol-1-yl-methyl)-acetanilide, 2-chloro-2'-methyl-6'-ethyl-N-(4-methoxy-pyrazol-1-yl-methyl)-acetanilide, 2-chloro-2',6'-dimethylpyrazol-1-yl-methyl)-acetanilide, 2-chloro-2'-methyl-6'-ethyl-N-(3-methylpyrazol-1-yl-methyl)-acetanilide, 2-chloro-2',6'-dimethyl-N-(1,2,4-triazol-1-yl-methyl)-acetanilide and 2-chloro-2',3',6'-trimethyl-N-(pyrazol-1-yl-methyl)-acetanilide.

9. A herbicidal agent as defined in claim 1, wherein A an is azole radical and the antagonist is selected from the group consisting of 5-dichloroacetyl-6-methyl-9-oxo-1,5-diazabicyclo[4.3.0]-nonane and 5-dichloroacetyl-3,3,6-trimethyl-9-oxo-1,5-diazabicyclo[4.3.0]nonane.

10. A herbicidal agent as defined in claim 1, wherein the acetanilide of the formula II is 2-chloro-2',6'-dimethyl-N-(pyrazol-1-yl-methyl)-acetanilide and wherein the antagonist of formula I is selected from the group consisting of 5-dichloroacetyl-6-methyl-9-oxo-1,5-diazabicyclo[4.3.0]-nonane and 5-dichloroacetyl-3,3,6-trimethyl-9-oxo-1,5-diazabicyclo[4.3.0]nonane.

11. A process as set forth in claim 3 wherein the crop plant is Indian corn.

12. A process as set forth in claim 4 wherein the crop plant is Indian corn.

* * * * *